United States Patent [19]

Embro

[11] Patent Number: 5,098,716
[45] Date of Patent: Mar. 24, 1992

[54] METHOD AND COMPOSITION FOR TREATING DISEASES HAVING A VIRAL ETIOLOGY

[76] Inventor: William J. Embro, 6320 S.W. 13th St., Gainesville, Fla. 32608

[21] Appl. No.: 572,179

[22] Filed: Aug. 23, 1990

[51] Int. Cl.⁵ .............................................. A61K 33/24
[52] U.S. Cl. ...................................... 424/650; 424/673
[58] Field of Search .......................... 424/650, 52, 673; 514/493

[56] References Cited

U.S. PATENT DOCUMENTS

| | | | |
|---|---|---|---|
| 2,749,213 | 6/1956 | Bruce | 23/50 |
| 4,267,164 | 5/1981 | Yeh et al. | 424/44 |
| 4,383,990 | 5/1983 | Coz et al. | 424/180 |
| 4,419,346 | 12/1983 | Stroz et al. | 424/151 |
| 4,431,631 | 2/1984 | Clipper et al. | 424/53 |
| 4,684,517 | 8/1987 | Clipper et al. | 424/52 |
| 4,952,392 | 8/1990 | Thame | 424/58 |

*Primary Examiner*—Glennon H. Hollrah
*Assistant Examiner*—B. M. Burn
*Attorney, Agent, or Firm*—McCormick, Paulding & Huber

[57] ABSTRACT

A method and composition for treating diseases having a viral etiology is provided. The method comprises administering either locally or systemically an antiviral effective, non-toxic amount of stannous fluoride. An isotonic, sterile injectable preparation of stannous fluoride for systemic administration is also disclosed.

5 Claims, No Drawings

METHOD AND COMPOSITION FOR TREATING DISEASES HAVING A VIRAL ETIOLOGY

BACKGROUND OF THE INVENTION

The present invention relates generally to the treatment of diseases having a viral etiology. More particularly, the present invention provides a method and a composition for treating such diseases with stannous fluoride.

Stannous fluoride (tin bifluoride) occurs naturally as a stable crystalline powder that is water soluble. For more than thirty-five years, this substance has been used in dental practice for the topical treatment of teeth to prevent carries and periodontal disease, and it has been well-established that stannous fluoride both inhibits dental plaque accumulation and promotes gingival health with fewer carries.

Stannous fluoride solutions and mouth rinses in strengths up to 30%$^w$/v have been shown to prevent recurrent dental carries; however, at present it is unclear what mechanism is responsible for this activity. Further, there is only limited information regarding the therapeutic effects of stannous fluoride on other disease states. In particular, the antiviral activity of this compound does not appear to have been investigated at all.

Accordingly, it is a principal object of the present invention to provide a method and compositions for treating viral diseases which affect both humans and other animals.

A more specific object of the present invention is to provide a method of treating immunocompromised patients who are highly susceptible to viral infections.

A further specific object of the invention is to provide a method for treating patients afflicted with cancers caused by ontogenic viruses.

SUMMARY OF THE INVENTION

These and other objects are achieved by the administration of an antiviral effective, non-toxic amount of stannous fluoride. The stannous fluoride may be administered locally or systemically depending on the nature of the disease state involved. In one preferred embodiment of the invention the stannous fluoride is incorporated into a gel base and administered locally during the prodromal stage of viral diseases caused by, for example, Herpes Zoster, Herpes Simplex and Papovivirus. In another preferred embodiment, the stannous fluoride is prepared as an isotonic, sterile injectable and then administered systemically to treat diseases caused by, for example, Herpes Simplex virus, Epstein-Barr virus, Cytomegalovirus, hepatitis virus, cold virus, flu virus, Varicella-Zoster virus, HIV I, HIV II and LAV viruses and ontogenic viruses.

PROPOSED MECHANISMS OF ACTION

Tin is listed with carbon, silicon, germanium and lead in group IV of the Periodic Table of the Elements. Compounds that form with carbon, silicon and germanium have strong covalent bonds; however, tin and lead form compounds having ionic or metallic bonds. Thus, compounds of tin and lead are more easily solubilized in both aqueous and non-aqueous solvents. This is especially true with regard to the compounds of tin and, in particular, stannous fluoride which is readily soluble in water at neutral pH according to the following reaction:

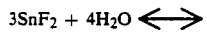

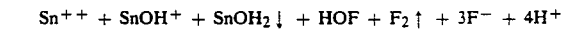

Because stannous fluoride is soluble at neutral pH and its components tin and fluorine are not associated with enzymatic activity, it appears likely that the chemical may interfere with the biochemistry of microorganisms.

Viral microorganisms are obligate intracellular parasites that require the active participation of the host cell's metabolic processes. Generally, viral inhibition can occur in two ways: by immunity or through the action of a chemotherapeutic antiviral agent. Immunity results when specific antibodies neutralize the virus before it enters the host cell. This can occur either before or after the virus has attached itself to associated receptors on the surface of the cellular membrane. It is likely that non-toxic interstitial concentrations of ionized $SnF_2$ assist in the body's immune response either by participating along with antibodies to directly neutralize free virus or by changing cell receptors for a particular virus to prevent attachment to the cellular membrane.

Unfortunately, many viruses, such as the AIDS virus, have the ability to quickly mutate which can substantially mitigate or even eliminate the body's immune response. Because such organisms cannot be "recognized" by the bodies immune system, they are able to evade destruction and successfully attach themselves to and then penetrate the cellular membrane.

It is also true, however, that many viruses require particular chemical substances to enter the host cell after they have successfully attached themselves to the cell membrane. For example, some viruses require the presence of calcium for transport across the cellular membrane. Moreover, the intracellular environment must contain specific chemical substances required for normal viral metabolism and replication.

Accordingly, the observed antiviral therapeutic activity of stannous fluoride may also result from ion concentration gradients of $Sn^{++}$ and $F^-$ which can passively or actively penetrate cell membranes via membrane transport systems to interrupt normal intracellular viral metabolism and reproduction and/or inhibit viral transport across the membrane.

DESCRIPTION OF THE PREFERRED EMBODIMENTS

A non-aqueous stannous fluoride gel is prepared by solubilizing $SnF_2$ in glycerin at approximately 150° F. for four hours. The resulting gel is a stable solution having an indefinite shelf life that is ideal for topical application to the skin and mucosal tissues.

Ten patients suffering with frequent recurrent Herpes Labailis were instructed to apply with Q-tip or finger a light coat of 0.4% stannous fluoride gel on the site of the lesion twice daily. Patients were contacted several months later to evaluate the efficacy of the treatment. No patient had a recurrent episode of the disease at the original site where the stannous fluoride gel was applied, and all indicated that the lesion regressed quickly with minimal pain.

All patients who applied the gel at the prodromal stage prevented outbreak to the viscular stage (a noticeable lesion) and the lesion was completely healed within two days. Patients who applied stannous fluoride gel at the viscular stage were immediately relieved of pain and the lesion was gone within three days. Stannous fluoride applied at both the prodromal and viscular stages prevented the scab stage. Only one patient applied the gel near the end stage of lesion (viscular entering scab stage) and it took six (6) days for healing.

Patients who used the available prescription and over-the-counter medications which do not contain stannous fluoride reported that, while some relief was obtained, it had no effect on recurrence of the lesion, with minimal effect on pain and healing time.

In a separate study, two patients having Herpes Zoster virus, a virus similar to Herpes Simplex, were instructed to apply the same 0.4% stannous fluoride gel. Within two days both patients felt less pain and their lesions had regressed.

The gel was also tested on a patient having Papovivirus. This patient was instructed to apply the gel four times a day for a two day period. The size of the wart was reduced from 10 mm to 6 mm over this period.

Since, as noted above, stannous fluoride is readily soluble in aqueous solutions, a sterile isotonic solution of the compound may be prepared for systemic administration. Administering stannous fluoride systemically is essential in combating non-localized viral infections such as AIDS, hepatitis, viral colds and flues, shingles and cancers caused by ontogenic viruses. Systemic administration of stannous fluoride is also an essential prophylactic measure in the treatment of in immunocompromised patients who are at high risk of contracting viral infections.

While preferred embodiments have been shown and described, various modifications and substitutions may be made without departing from the spirit and scope of the invention. Accordingly, it is to be understood that the present invention has been described by way of example and not by limitation.

I claim:

1. A method for treating herpes virus infections in humans and other animals comprises administering thereto an antiviral effective, non-toxic amount of stannous fluoride in combination with a pharmaceutically acceptable carrier.

2. The method of claim 1 further characterized in that the stannous fluoride is first incorporated into a gel base and then administered topically.

3. The method of claim 2 further characterized in that the herpes virus infections are caused by Herpes Zoster, Herpes Simplex and Papovivirus.

4. The method of claim 2 further characterized in that the stannous fluoride is administered as a 0.4% gel.

5. The method of claim 3 further characterized in that the stannous fluoride is administered during the prodromal period of the diseases.

* * * * *